(12) United States Patent
Henot et al.

(10) Patent No.: US 7,893,250 B2
(45) Date of Patent: Feb. 22, 2011

(54) DEMETHYLATED AND/OR OXIDIZED MEMBRANE DNA

(75) Inventors: Frederic Henot, Brussels (BE); Thierry Legon, Korbeek Lo (BE); Nadine Questiaux, Louvain-la-Neuve (BE)

(73) Assignee: BioTech Tools, Brussels (BE)

( * ) Notice: Subject to any disclaimer, the term of this patent is extended or adjusted under 35 U.S.C. 154(b) by 29 days.

(21) Appl. No.: 11/878,800

(22) Filed: Jul. 26, 2007

(65) Prior Publication Data

US 2008/0075735 A1 Mar. 27, 2008

Related U.S. Application Data

(62) Division of application No. 10/270,160, filed on Oct. 15, 2002, now abandoned.

(51) Int. Cl.
*C07H 21/00* (2006.01)
*C12Q 1/68* (2006.01)

(52) U.S. Cl. .......................... 536/25.4; 435/6
(58) Field of Classification Search ....................... None
See application file for complete search history.

(56) References Cited

U.S. PATENT DOCUMENTS 6,057,097 A    5/2000   Servais et al.

OTHER PUBLICATIONS

Gasparro et al. Cell membrane DNA: A new target for psoralen photoadduct formation. Photochemistry and Photobiology (1990) 52(2): 315-321.*
Williams et al. Oxidative DNA damage: Endogenous and chemically induced. Regulatory Toxicology and Pharmacology (2000) 32: 283-292.*
Cano et al. Neither ERK nor JNK/SAPK MAP kinase subtypes are essential for histone H3/HMG-14 phosphorylation or c-fos and c-jun induction. Journal of Cell Science (1995) 108: 3599-3609.*
Ramanathan et al. Enhanced DNA repair synthesis in hyperacetylated nucleosomes. Journal of Biological Chemistry (1989) 264(19): 11026-11034.*
Chan et al. Different mechanisms by which anti-DNA MoAbs bind to human endothelial cells and glomerular mesangial cells. Clinical Experimental Immunology (1992) 88: 68-74.*
Ara et al. Polynucleotide specificity of anti-reactive oxygen species (ROS) DNA antibodies. Clinical Experimental Immunology (1993) 94: 134-139.*
Wei et al. In Vivo Formation of Oxidized DNA Bases in Tumor Promoter-treated Mouse Skin. Cancer Research (1991) 51: 4443-4449.*

Wei et al. In vivo formation of oxidized bases in tumor-promoter treated mouse skin. Cancer Research (1991) 51: 4443-4449.*
Ma et al. DNA excision repair proteins and Gadd45 as molecular players for active DNA demethylation. Cell Cycle (2009) 8(10): 1526-1531.*
Liu et al. PUVA (8-Methoxy-Psoralen Plus Ultraviolet A) Induces the Formation of 8-Hydroxy-29 Deoxyguanosine and DNA Fragmentation in Calf Thymus DNA and Human Epidermoid Carcinoma Cells. Free Radical Biology and Medicine (1999) 27(1/2): 127-133.*
Bennett et al. DNA Binding to Human Leukocytes: Evidence for a Receptor-mediated Association, Internalization, and Degradation of DNA. Journal of Clinical Investigation (1985) 76: 2182-2190.*
Frenkel et al., "Enhanced antibody titers to an oxidized DNA base in inflammatory and neoplastic diseases", *Experimental Dermatology*, vol. 1, 242-247 (1992).
Frenkel et al., Recognition of Oxidized DNA Bases by Sera of Patients With Inflammatory Diseases, *Free Radical Biology & Medicine*, vol. 14, 483-494 (1993).
Servais et al., Diagnostic specificities and sensitivities of anti dsDNA, anti membrane DNA and anti nucleosomes autoantibodies, *Scand J Clin Lab Invest*, vol. 61, 61-67 (2001).
Servais et al., "Evidence of autoantibodies to cell membrane associated DNA (cultured lymphocytes): a new specific marker for rapid identification of systemic lupus erythematosus", *Ann Rheum Dis*, vol. 57, 606-613 (1998).
Yamashita et al., "Tyrosine phosphorylation is crucial for growth signaling by tissue inhibitors of metalloproteinases (TIMP-1 and TIMP-2)", *FEBS Letters*, vol. 396, 103-107 (1996).
Mazurier, et al., "Développement Préclinique du concentré de facteur Willebrand vWF SD-35-DH", *Sang Thrombose Vaisseaux*, vol. 11. No. Spezial, (Oct. 1999), XP 000925923-, pp. 30-35. (English-language abstract).
Comacchia et al., "Hydralazine and Procainamide Inhibit T Cell DNA Methylation and Induce Autoreactivity", *Journal of Immunology*, vol. 140, No. 7, (Apr. 1988), pp. 2197-2200.
Meinke et al., "Physical Properties of Cytoplasmic Membrane-associated DNA", *J. Mol. Biol.* vol. 78 (1973)pp. 43-56.
Kuo et al., "Localization of Cytoplasmic-Membrane-associated DNA in Human Chromosomes", *Proc. Nat. Acad. Sci USA*. vol. 72, No. 12 (Dec. 1975), pp. 5004-5006.

(Continued)

*Primary Examiner* — Young J Kim
*Assistant Examiner* — Angela M Bertagna
(74) *Attorney, Agent, or Firm* — Jacobson Holman PLLC

(57) ABSTRACT

A process for the preparation of oxidized and/or demethylated antigens comprising the steps of
  treating a cell with a stress factor selected from the group consisting of UV-radiation, oxidizing reagents, heavy metal salts, drugs, nucleoside and nucleotide analogs, and enzyme inhibitors
  lyses of the cell to give a cell lysate
  purification of oxidized and/or demethylated antigens from the cell lysate.

2 Claims, No Drawings

OTHER PUBLICATIONS

Meinke et al., "Reassociation and Dissociation of Cytoplasmic Membrane-Associated DNA", *J. Mol. Biol.* vol. 86, (1974), pp. 757-773.

Du et al., "Exposure of Hep-2 Cells to Stress Conditions Influences Antinuclear Antibody Reactivity", *Clinical and Diagnostic Laboratory Immunology*, (Mar. 2002), pp. 287-294. vol. 9, issue 2.

Perez et al., "DNA Associated with the Cell Membrane is Involved in the Inhibition of the Skin Rejection Response Induced by Infusions of Photodamaged Alloreactive Cells that Mediate Rejection of Skin Allograft", *Photochemistry and Photobiology*, vol. 55. No. 6, (1992), pp. 839-849.

Ara et al., "Polynucleotide Specificity of Anti-reactive Oxygen Species (ROS) DNA Antibodies", *Clin. Exp. Immunol.* (1993) pp. 94:134-139.

Krieg et al., "CpG DNA: A Pathogenic Factor in Systemic Lupus Erythematosus?", *Journal of Clinical Immunology*, vol. 15, No. 6, (1995), pp. 284-292.

Huck et al., "Abnormal DNA methylation and deoxycytosine-deoxyguanine content in nucleosomes from lymphocytes undergoing apoptosis", *The FASEB Journal*, vol. 13, (Aug. 1999), pp. 1415-1422.

Weitzman et al., "Free Radical Adducts induce alterations in DNA cytosine methylation", *Proc. Natl. Acad. Sci. USA, Biochemistry*, vol. 91 (Feb. 1994), pp. 1261-1264.

Bialkowski et al., "A novel assay of 8-oxo-2'-deoxyguanosine 5'-triphosphate pyrophosphohydrolase (8-oxo-dGTPase) activity in cultured cells and its use for evaluation of cadmium(II) inhibition of this activity", *Nucleic Acids Research*, vol. 26. No. 13, (1998), pp. 3194-3201.

Hodges et al., "Down-regulation of the DNA-repair endonuclease 8-oxo-guanine DNA glycosylase 1 (hOGG1) by sodium dichromate in cultured human A549 lung carcinoma cells", *Carcinogenesis*, vol. 23. No. 1, (2002), pp. 55-60.

Tasneem et al., "Binding of SLE Autoantibodies to Native poly(I), ROS-poly(I) and Native DNA: A Comparative Study", *Journal of Autoimmunity*, vol. 17, (2001), pp. 199-205.

Rosen et al., "8-Oxodeoxyguanosine Formation in the DNA of Cultured Cells After Exposure to $H_2O_2$ Alone or with UVB or UVA Irradiation", *Photochemistry and Photobiology*, No. 64(1), (1996), pp. 177-122.

* cited by examiner

DEMETHYLATED AND/OR OXIDIZED MEMBRANE DNA

This is a divisional of Ser. No. 10/270,160, filed Oct. 15, 2002, which is now abandoned.

FIELD OF THE INVENTION

The present invention relates to a process for the preparation of oxidized and/or demethylated cytoplasmic membrane-associated DNA (cmDNA) or membrane DNA (mDNA) and oxidized and/or demethylated mDNA.

It further relates to a cell comprising the oxidized and/or demethylated membrane DNA and the diagnostic and pharmaceutical use of the oxidized and/or demethylated membrane DNA and the cells comprising such mDNA.

BACKGROUND OF THE INVENTION

U.S. Pat. No. 6,057,097, incorporated per reference, disclosed markers for pathologies comprising an autoimmune reaction and markers for inflammatory diseases.

As disclosed in this document, numerous pathologies comprising an autoimmune reaction and inflammatory diseases have an uncertain or unknown etiology and may have a multifactor origin.

The diagnosis of some of these diseases is difficult or uncertain. One disease especially mentioned in this document is systemic lupus erythematosus (SLE). Prior to U.S. Pat. No. 6,057,097 it had not been possible to provide a sufficient specific antigenic structure to obtain a reliable diagnosis both in specificity and sensitivity for the mentioned pathologies, especially SLE.

U.S. Pat. No. 6,057,097 solves the problem by providing an antigenic structure named cytoplasmic-membrane associated DNA (cmDNA) or membrane DNA (mDNA).

This antigen is recognized by antibodies present in biological fluids of subjects suffering from the mentioned diseases. This antigenic structure is prepared from cells especially from β-lymphocytes such as Wil-2 cells.

It is the aim of the present invention to provide an improved antigenic structure and thereby an improved diagnostic tool showing increased specificity and sensibility.

A further aim is to provide a screening method for pharmaceutical substances useful in the treatment of autoimmune diseases and/or inflammations.

A further aim is to provide a pharmaceutical composition.

SUMMARY OF THE INVENTION

According to the invention, the antigenic structure is prepared by a process for the preparation of membrane DNA in an oxidized and/or demethylated condition.

This process comprises the steps of
  treating a cell with a stress factor selected from the group consisting of UV-irradiation, oxidizing reagents, heavy metal salts, drugs, nucleoside and nucleotide analogs, enzyme inhibitors and pH-shift
  lyses of the cell to give a cell lysate
  purification of oxidized and/or demethylated mDNA from the cell lysate.

It is believed that treatment with stress factors increases the amount of oxidized membrane DNA and/or increases demethylation of membrane DNA in the cell. Afterwards, the mDNA is isolated in a similar manner as previously known from U.S. Pat. No. 6,057,097.

"Oxidized and/or demethylated mDNA" is mDNA that is either oxidized, or demethylated or both.

"Oxidized membrane DNA" is membrane DNA comprising more oxidized nucleotides in relation to mDNA from cells not treated with stress factors.

The most abundant oxidized nucleotide is 8-oxo-7,8-dihydro-2'-deoxyguanosine (8-oxo-dG). The oxidized mDNA comprises preferably more than 0.5%, more preferred more than 1%, most preferred more than 3% of all guanosine in an oxidized form.

"Demethylated mDNA" is an mDNA comprising less methylated nucleotides than mDNA prepared from the cells without treatment with a stress factor.

The methylated nucleotide is usually cytosine. Such methylation mostly occurs in the context of CpG dinucleotides in vertebrates and is often associated with transcriptional repression.

Preferable the amount of 5-methylated cytosine is less than 90% of untreated mDNA, more preferably 50% or less and more preferred 30% or less.

Suitable stress factors are for example dichromate, hydrogen peroxide, permanganate, quinidine, D-pencillamine, hydralazine, procainimide, RNA/DNA metabolites, nucleoside and nucleotide analogs such as 5-aza-cytidine, 5-aza-2'-deoxycytidine, inhibitors of DNA methylases, inhibitors of histone deacetylases such as butyrates or trichostatin A, inhibitors of histone arginine and histone lysine methyltransferases, inhibitors of protein kinases such as staurosporine or calphostin C or K-252a or H-89, activators of protein kinases such as phorbol esters or bryostatin 1, inhibitors of protein phosphatases such as calyculin A or okadaic acid, inhibitors of poly(ADP-ribose) polymerase such as 3-aminobenzamide or m-Iodobenzylguanidine hemisulfate, inhibitors of ubiquitin conjugating enzymes such as methylated ubiquitin, inhibitors of ubiquitin C-terminal hydrolase such as ubiquitin aldehyde, inhibitors of enzymes involved in correction of replicational errors and/or spontaneous DNA damage such as cadmium ions, inhibitors of N-glycosylation such as tunicamycin, inhibitors of 20S or 26S proteasomes such as lactacystin, inhibitors of farnesylation such as alpha-hydroxyfarnesylphosphonic acid, inhibitors of geranylgeranylation, inhibitors of protein methylation such as ebelactone B, inhibitors of catalase, inhibitors of superoxide dismutase, inhibitors of glutathione peroxidase, or combinations thereof.

A further suitable stress factor is a pH-shift. A pH-shift is a change of the pH of the environment of at least 0.2 pH-units, preferably 0.4 pH-units.

A further suitable stress factors is for example UV irradiation. UV irradiation is preferably combined with oxidizing reagents.

Suitable oxidizing reagents are for example $H_2O_2$ or molecular oxygen.

From molecular oxygen, active species such as superoxide radical ($O_2^-$.) and hydroxyl radical (HO.) can be obtained, see for example "proceedings of the society for experimental biology and medicine" 1999, pages 246 to 252.

Suitable heavy metal salts are cadmium salts, chrome salts or mixtures thereof. They can be used alone or in combination with the oxidizing reagents for example $O_2$ or $H_2O_2$.

A further embodiment of the present invention is the oxidized and/or demethylated membrane DNA (mDNA) obtainable according to the method of the invention.

Such oxidized and/or demethylated membrane DNA is useful as an antigenic structure in a diagnostic test of autoimmune diseases.

In a further embodiment the mDNA or fragments of the mDNA are further associated with DNA binding proteins, most preferably, with histones.

These DNA binding proteins may be hypo- or hyperacetylated, hypo- or hyperphosphorylated, hypo- or hypermethylated, hypo- or hyperubiquitinated, hypo- or hyper-(poly-ADP-ribosylated) or hypo- or hyperglycosylated or combinations thereof.

A further embodiment of the present invention are cells comprising membrane DNA of the present invention.

In a preferred embodiment of the invention, the cells are selected from the group of leucocytes, especially neutrophils, and/or B-lymphocytes and/or lymphoblastoid cells and/or monocytes.

Such cells can be obtained by a process comprising the step of treating a cell with a stress factor selected from the group consisting of UV-irradiation, oxidizing reagents, heavy metal salts, drugs, nucleoside and nucleotide analogs, enzyme inhibitors and pH-shift.

Suitable stress factors are disclosed supra.

A further embodiment of the invention is a diagnostic agent comprising oxidized and/or demethylated membrane DNA, fragments of this mDNA or cells comprising the oxidized and/or demethylated membrane DNA.

This diagnostic agent can be used in different diagnostic tests.

In one embodiment, the present invention covers therefore a process for the detection of an autoimmune disease comprising the steps of
- bringing a biological fluid of an animal containing antibodies into contact with the diagnostic agent of the invention.
- measuring binding of said antibodies with said diagnostic agent wherein binding indicates an autoimmune disease of the animal.

In a preferred embodiment, the diagnostic agent is in the form of cells and the cells are attached to a solid support prior to bringing the biological fluid in contact with the diagnostic agent. Such an attachment may be covalently or not covalently, either through ligand/receptor or ligand/protein interaction or biotinylated cells/(strept)avidin; lectin/antilectin or through a covalent binding between an activated solid support and amino, acidic or sulfhydryl groups or carbohydrates or oxidized carbohydrates of the cell surface.

In a second embodiment, the present invention covers a process for the in-vitro detection of an autoimmune disease comprising the steps of
- bringing a biological sample of an animal containing cells into contact with antibodies directed against the oxidized and/or demethylated mDNA of claim 4
- measuring binding of said antibodies with said cells
- wherein binding indicates a autoimmune disease of the animal.

Preferably these diagnostic test are done in-vitro.

Such diagnostic tests are also useful with other antigens, that are chemically modified by treating a cell with a stress factor.

In a suitable test, the cells could be used to identify binding of antibodies from the biological fluids, especially blood or sera to the cells.

Alternatively, the oxidized and/or demethylated mDNA could be used in a test system, for example in an ELISA to identify binding.

It is a further embodiment of the invention to use the diagnostic agent to detect binding of antibodies to membrane DNA. Such a binding indicates an autoimmune disease of the animal.

A further embodiment, the present invention provides a method for identifying drugs by a screening method. This screening method comprises measuring the binding of antibodies to the oxidized or demethylated mDNA or fragments thereof or cells comprising oxidized or demethylated mDNA. The influence of potential substances on the binding of the antibodies indicates whether or not such substances are useful pharmaceutical compositions.

Yet another embodiment of the present invention is a pharmaceutical formulation comprising the oxidized or demethylated mDNA or fragments or cells comprising oxidized or demethylated DNA. Such a pharmaceutical composition could be used to detract autoimmune antibodies of a patient from structures of the patient, thereby reducing or healing the disease.

This pharmaceutical formulation could also be used in form of a vaccine.

Therefore, the use of the pharmaceutical formulation for treating autoimmune diseases in animal is also part of the invention.

The present invention is further explained by the following, non-limiting examples.

EXAMPLES

Cell Culture

The cell line of human lymphoblastoid B (Wil2 NS) obtained from ICN Flow Laboratories (ECACC No 90112121) is maintained in RPMI 1640 supplemented with 10% foetal bovine serum (heat inactivated and tested for the absence of mycoplasma), L-glutamine and 1% penicillin-streptomycin, in an humid oven at 37° C. and 5% $CO_2$.

Sera

The sera are obtained from patients affected by several inflammatory diseases or pathologies having an auto-immune reaction and from normal individuals. The sera are obtained from centrifuged coagulated blood and held at −20° C. until use.

In all the experiments described below, sera of SLE patients that are positive in the test according to U.S. Pat. No. 6,057,97 are always positive whatever the cell treatment.

LED 0 means SLE patients, having at least four of the SLEDAI criteria, of whom sera diluted 1/30 do not give a positive pattern in the test of U.S. Pat. No. 6,057,097.

RF is used for "sera from patients affected by several inflammatory diseases or pathologies but not SLE".

In-Vitro Oxidation of mDNA

Wil2 NS cells are washed three times with Hank's solution (Gibco BRL) and re-suspended at $0.25 \times 10^6$ cells/mL in HBSS and subsequently spotted on glass slides divided into 20 μL/wells. After drying at 37° C. during 2 hours, in an oven, the cells are fixed for 3 minutes in methanol. The cells are then incubated for 30 minutes at room temperature in the presence of goat anti-human albumin serum (Dia-Sorin) diluted at 1/35 in 30 μL PBS. Slides are then washed in PBS.

The slides were exposed to 1% of hydrogen peroxide in PBS and immediately irradiated with UVB at 254 nm during 1 hour under a UV-CAMAG lamp. Irradiation was performed at room temperature in the dark at 13 cm of the slides.

The slides are incubated for 30 minutes in the presence of different patients sera diluted 1/10 in PBS/Tween 0.05% (cell culture grade) at 20 μl/well and washed again with PBS. The slides are further incubated for 30 minutes in the dark in the presence of 30 μL of a fluorescein-conjugated goat anti-human IgG (Inova) dialyzed overnight at 4° C. in Slide-A-Lyser 10,000 MWCO (Pierce) and then centrifugated three times on a Centricon MY-10 (Millipore). A final wash of the slides is performed with PBS alone, followed by PBS containing Evans Blue as counterstain. Finally, slides are mounted in glycerin/PBS (1:1) pH 8.4, and visualized by means of UV immersion (Nikon).

Results:

In-vitro oxidation was performed with $H_2O_2+UV_{254\,nm}$, and 45 sera were tested (5 healthy subjects, 10 auto-immuns, and 30 rheumatoid arthritis).

| Sera, dilution 1/10 | No oxidation U.S. Pat. No. 6,057,097 | | oxidation | |
|---|---|---|---|---|
| | positive | negative | positive | negative |
| LED 0 | 8 | 2 | 7 | 3 |
| RF | 32 | 13 | 3 | 42 |

Obviously, in-vitro oxidation of mDNA increases specificity and sensibility of the test, and allows to identify more SLE patients.

In-Vivo Oxidation of mDNA

A pool of cadmium acetate (Cd), sodium dichromate (Cr) and hydrogen peroxide ($H_2O_2$) was added (at the final concentrations of 10 pM, 10 μM and 20 μM respectively) to the culture 17 hours 30 minutes prior to the removing of cells in the growing logarithmic phase. The preparation, at a density of 1.0 to $1.5 \times 1b^6$ cells/mL, was assessed for viability both before and at the end of the experiment by trypan Biue exclusion. Viability must be more than 95%.

Wil2 NS cells are washed once in PBS (Phosphate buffered saline, 10 mM, pH 7.4), then once in PBS supplemented with ATP at a final concentration of 500 μM. After that, they are incubated for 30 minutes at room temperature in the presence of goat anti-human albumin (Dia-Sorin) diluted at 1/35 in PBS. Cells are then collected by centrifugation, and re-suspended at $0.2 \times 10^6$ cells/mL and subsequently spotted on glass slides divided into 20 μL/wells After drying at 37° C. during 2 hours in an oven, the cells are fixed for 3 minutes in methanol and washed once in PBS (Phosphate buffered Saline, 10 mM, pH 7.4).

They are incubated for 30 minutes in the presence of different patients sera diluted 1/20 in PBS/Tween 0.05% (cell culture grade) at 20 μL/well and washed again with PBS. The slides are further incubated for 30 minutes in the dark in the presence of 30 μL of a mixture of fluorescein-conjugated goat F(ab₂)' anti-human IgG (Sigma, dilution 1/60) and fluorescein-conjugated goat IgG anti-human IgM (Sigma, dilution 1/70). A final wash of the slides is performed with PBS alone, followed by PES containing Evans Blue as counterstain. Finally, slides are mounted in glycerin/PBS (1:1), pH 8.4, and visualized by means of UV immersion microscope (Nikon), magnification (40×).

Results:

When cells growth occurs in RPMI 1640 supplemented with 10% FBS and the various products, only 10 of 327 sera from patients affected by several inflammatory diseases or pathologies but not SLE, give a positive pattern, and 15 of 31 sera referenced as "LED 0" give a positive pattern. The test has a specificity of 97% and a sensibility of 82%.

When cells growth occurs in a serum-free medium (AIMV 5, Life Technologies) and the various products, only 6 of 347 sera from patients affected by several inflammatory diseases or pathologies but not SLE, give a positive pattern, and 18 of 31 sera referenced as "LED 0" give a positive pattern. The test has a specificity of 98.3% and a sensibility of 84%.

In-Vivo Inhibition of DNA Methylases

5-Aza-cytidine was added at the final concentrations of 1.0 μM to the culture 17 hours 30 minutes prior to the removing of cells in the growing logarithmic phase. The preparation, at a density of 1.5 to 1.8 to $2.0 \times 10^6$ cells/ml, was assessed for viability both before and at the end of the experiment by trypan Blue exclusion. Viability must be more than 95%.

The slides are incubated for 30 minutes in the presence of different patients sera diluted 1/20 in PBS/Tween 0.05% (cell culture grade) at 20 μL/well and washed again with PBS.

The slides are further incubated for 30 minutes in the dark in the presence of 30 μl of a mixture of fluorescein-conjugated goat F(ab₂)' anti-human IgG (Sigma, dilution 1/60) and fluorescein-conjugated goat IgG anti-human IgM (Sigma, dilution 1/70).

Results:

| sera | quantity | dilution | Ox | AzaC |
|---|---|---|---|---|
| LED 0 | 3 | 1/10 | 3 | 3 |
| RF | 7 | 1/10 | 7 | 2 | ox: Cr + Cd + $H_2O_2$;
AzaC: 5-aza-cytidine.

Demethylated mDNA is also a good antigen and is well recognized by anti-mDNA antibodies of SLE patients sera. Specify is increased a well as sensibility because sera can be diluted 1/10 instead of 1/30.

It should be noticed here that 6 of the 7 RF sera are those that were "positive" in the experiment described above.

In-Vivo Inhibition of Histone Deacetylation

Sodium butyrate was added at the final concentrations of 1.0 mM to the culture medium (serum-free medium AIMV 5, Life Technologies) 17 hours 30 minutes prior to the removing of cells in the growing logarithmic phase. The preparation, at a density of 1.5 to $1.8 \times 10^6$ cells/ml, was assessed for viability both before and at the end of the experiment by trypan Blue exclusion. Viability must be more than 95%

The slides are incubated for 30 minutes in the presence of different patients sera diluted 1/20 in PBS/Tween 0.05% (cell culture grade) at 20 μL/well and washed again with PBS.

The slides am further incubated for 30 minutes in the dark in the presence of 30 μl of a mixture of fluorescein-conjugated goat F(ab₂)' anti-human IgG (Sigma, dilution 1/60) and goat IgG anti-human IgM (Sigma, dilution 1/70).

Results:

| sera | quantity | dilution | NaBut |
|---|---|---|---|
| LED 0 | 7 | 1/20 | 7 |
| RF | 15 | 1/20 | 1 |

NaBut: sodium butyrate

It seems that controlling histone hyperacetylation improves the selectivity of the test. Hence, membrane DNA might be associated with hyperacetylated histones on the cell surface (nucleosome-like structures)

Presence of 8-oxo-2'-deoxyguanosine

The $H_2O_2$-UV irradiated slides or slides produced with cells grown in presence of either $Cd+Cr+H_2O_2$ or 5-azacytidine, or sodium butyrate are incubated overnight at 4° C. in the presence of 30 µl of an anti-8-oxo-dG mouse monoclonal antibody (Gentaur) diluted 1/100 in 10 mM Tris-HCl, pH 7.5, 10% Foetal Bovine Serum. The slides are washed once in PBS and then incubated for 40 minutes in the presence of a goat anti-mouse IgG1 antibody (southern Biotechnology Associates, Inc) diluted at a concentration of 0.1 µg/1×$10^6$ cells in PBS.

A final wash of the slides is performed in PBS and slides are mounted in glycerin/PBS pH 8.4 prior visualization by means of UV immersion microscope.

Results:

A positive pattern 5 represented by a cell membrane green punctuate pattern. 8-Oxo-dG is shown to be present at the cell surface when oxidation of mDNA was performed either in-vivo ($Cd+Cr+H_2O_2$) or in-vitro ($H_2O_2$+UV) according to the method described supra.

A positive pattern is also shown when cells were grown in the presence of 5-aza-cytidine but not in presence of sodium butyrate.

Presence of 5-methylcytosine

The slides produced with cells grown in presence of either $Cd+Cr+H_2O_2$ or 5-azacytidine, or sodium butyrate are incubated overnight at 4° C. in the presence of 30 µl of an anti-5 methylcytosine sheep antibody (Abcam, Ab1884) diluted 1/100 in PBS. The slides are washed once in PBS and then incubated for 15 seconds in the presence of 30 µl of NaOH $7\times10^{-5}$ N. After washing with PBS, the slides are finally incubated 30 minutes in the presence of a donkey anti-sheep IgG antibody (southern Biotechnology Associates, Inc) diluted at a concentration of 0.1 µg 1 1×$10^6$ cells in PBS.

A final wash of the slides is performed in PBS and slides are mounted in glycerin/PBS pH 8.4 prior visualization by means of UV immersion microscope.

Results:

A positive pattern to identify 5-methylcytosine within the cells is represented by an intracellular green fluorescence.

Strong overall methylation of DNA occurred for cells grown in presence of either $Cd+Cr+H_2O_2$ or sodium butyrate but not in the presence of 5-aza-cytidine, even if intracellular green fluorescence of cells treated by sodium butyrate is not as strong as the first case.

The invention claimed is:

1. A process for the preparation of oxidized cytoplasmic membrane-associated DNA (cmDNA) comprising the steps of
    treating a lymphocyte with a stress factor selected from the group consisting of hydrogen peroxide, dichromate, permanganate, and a cadmium salt,
    lysing the lymphocyte to produce a cell lysate, and
    purifying the oxidized cmDNA from the cell lysate.
2. The process of claim 1, wherein the oxidized cmDNA is associated with nucleic acid binding proteins.

* * * * *

UNITED STATES PATENT AND TRADEMARK OFFICE
CERTIFICATE OF CORRECTION

| | | |
|---|---|---|
| PATENT NO. | : 7,893,250 B2 | |
| APPLICATION NO. | : 11/878800 | |
| DATED | : February 22, 2011 | |
| INVENTOR(S) | : Henot et al. | |

It is certified that error appears in the above-identified patent and that said Letters Patent is hereby corrected as shown below:

Column 5, line 33: "of 10 pM" should read --of 10 µM--

Column 5, line 36: "of 1.0 to 1.5×1b$^6$" should read --of 1.0 to 1.5×10$^6$--

Column 5, line 57: "washed again with PBS" should read --washed again with PBs--

Column 6, line 4: "(AIMV 5,) should read --(AIMV)--

Column 6, line 38: "Specifity" should read --Specificity--

Column 6, line 44: "AIMV 5" should read --AIMV--

Column 6, line 54: "The slides am" should read --The slides are--

Column 7, line 13: "southern Biotechnology" should ready --Southern Biotechnology--

Column 8, line 7: "southern Biotechnology" should ready --Southern Biotechnology--

Signed and Sealed this
Third Day of July, 2012

David J. Kappos
*Director of the United States Patent and Trademark Office*